(12) United States Patent
Shirai et al.

(10) Patent No.: US 6,413,541 B1
(45) Date of Patent: Jul. 2, 2002

(54) DISINTEGRATING TABLET IN ORAL CAVITY AND PRODUCTION THEREOF

(75) Inventors: Yoshimi Shirai, Suita; Kiyomi Sogo, Osaka; Kazuyoshi Ogasawara, Kitakatsuragi-gun; Yutaka Higashi, Osaka; Yasuhiko Nakamura, Takarazuka, all of (JP)

(73) Assignee: Dainippon Pharmaceutical Co., Ltd., Osaka-fu (JP)

( * ) Notice: Subject to any disclaimer, the term of this patent is extended or adjusted under 35 U.S.C. 154(b) by 15 days.

(21) Appl. No.: 09/614,182

(22) Filed: Jul. 11, 2000

(51) Int. Cl.⁷ .............................. A61K 9/20; A61F 13/00
(52) U.S. Cl. ...................... 424/435; 424/465; 424/464; 514/772.3; 514/774; 514/777; 514/781
(58) Field of Search ................................. 424/464, 465, 424/435, 439, 440, 441

(56) References Cited

U.S. PATENT DOCUMENTS

| | | | |
|---|---|---|---|
| 4,305,502 A | | 12/1981 | Gregory et al. |
| 4,371,516 A | | 2/1983 | Gregory et al. |
| 5,466,464 A | | 11/1995 | Masaki et al. |
| 5,501,861 A | | 3/1996 | Makino et al. |
| 5,576,014 A | * | 11/1996 | Mizumoto et al. .......... 424/435 |
| 5,654,003 A | | 8/1997 | Fuisz et al. |
| 5,837,285 A | | 11/1998 | Nakamichi et al. |

FOREIGN PATENT DOCUMENTS

| | | |
|---|---|---|
| JP | 8-19589 | 1/1996 |
| JP | 8-19590 | 1/1996 |
| JP | 8-291051 | 11/1996 |
| JP | 9-48726 | 2/1997 |
| JP | 9-316006 | 12/1997 |
| WO | 93/13758 | 7/1993 |
| WO | 95/34290 | 12/1995 |
| WO | 95/34293 | 12/1995 |

* cited by examiner

*Primary Examiner*—James M. Spear
(74) *Attorney, Agent, or Firm*—Wenderoth, Lind & Ponack, LLP

(57) ABSTRACT

Method for producing intrabuccally disintegrating tablets, which comprises the following Steps (a), (b) and (c), wherein a medicament is mixed before granulation or tabletting: (a) a step of dissolving at least one saccharide having a high solubility in water and at least one water-soluble binder in water alone or in water and an alcohol; (b) a step of mixing the solution obtained in above Step (a) with at least one excipient, granulating, drying, and tabletting the mixture under a low compression pressure; (c) a step of aging the tablets obtained in Step (b), and intrabuccally disintegrating tablets produced by the above method are provided. The method of the present invention is a simple method for producing intrabuccally disintegrating tablets in large scale without using specific facility, and by which intrabuccally disintegrating tablets showing good disintegrating property in oral cavity as well as having sufficient strength can be obtained.

30 Claims, No Drawings

DISINTEGRATING TABLET IN ORAL CAVITY AND PRODUCTION THEREOF

BACKGROUND OF THE INVENTION

The present invention relates to a method for production of a tablet readily disintegrating in the oral cavity (hereinafter, referred to as "intrabuccally disintegrating tablet"), and to an intrabuccally disintegrating tablet which is produced by said method.

With the increase in the population of aged people, a pharmaceutical dosage form being capable of being easily taken by persons advanced in age has been desired, but many of pharmaceutical dosage forms for oral administration are conventional forms of tablets or capsules at the present, and it is not easy for aged people to swallow these dosage forms. Besides, these conventional dosage forms are often difficult to be swallowed by children or patients having poor swallowing capability. Moreover, powders or granules have also defects, for example, they need extra attention when being unpacked, or they adhere to the oral cavity when taken, and hence, they are not satisfactory enough for aged people, children or patients having poor swallowing capability, either. In order to overcome these problems, there have been studied on some tablets being easily taken without using water and being very easy for handling.

U.S. Pat. Nos. 4,371,516 and 4,305,502 (corresponding to JP-B-62-50445) disclose a method for producing a tablet, which comprising charging a suspension of a medicament, a saccharide and a gellant into a blister package of PTP (Press Through Package), subliming the water therefrom by lyophilization, and formulating tablets in said blister package. U.S. Pat. No. 5,466,464 (corresponding to PCT publication WO 93-12769) discloses a method for producing a tablet which comprises charging a suspension of a medicament, mannitol and agar into a blister package of PTP, subliming the water therefrom by drying under reduced pressure, and formulating tablets in said blister package.

U.S. Pat. No. 5,837,285 (corresponding to Japanese Patent No. 2650493, and PCT publication WO 93-15724) discloses a rapidly soluble tablet rapidly dissolving in the oral cavity, which is produced by compressing wet granules containing mainly saccharides granulated with water, and followed by drying thereof, and U.S. Pat. No. 5,501,861 (corresponding to Japanese Patent Publication JP-A-5-271054) discloses a method for producing an intrabuccally disintegrating tablet, which comprises compression-molding a mixture containing a barely sufficient amount of water to moisten the surface of particles. These methods are generally known as "wet-tabletting method".

JP-A-8-291051 and JP-A-9-48726 disclose a method for producing an intrabuccally disintegrating tablet, which comprising compression-molding a powder containing mainly a saccharide and a water-soluble binder under a low pressure, wetting the resulting tablets by placing them under humid, and drying them (hereinafter, occasionally referred to as "humidification method").

WO 93-13758 (corresponding to Japanese Patent No. 2640570) discloses a method for producing a tablet of increased strength, which comprises the steps of compression-molding a powder containing a water-soluble meltable binder such as polyethylene glycol with a low pressure, melting said water-soluble meltable binder in the resulting tablet at a temperature higher than a melting point of said water-soluble meltable binder, followed by solidifying said water-soluble meltable binder (hereinafter, occasionally referred to as "heat-melting method").

JP-A-9-316006 discloses a rapidly dissolving and disintegrating solid preparation in the oral cavity having a fresh feeling, which is improved by containing erythritol and a small amount of a solid organic acid.

On the other hand, as specific methods, WO 95-34290 discloses a method for producing a tablet, which comprises preparing shearform matrix in sheared cotton candy amorphous, making it flowable compactible microparticulates, followed by compacting the resultant to give tablets, and WO 95-34293 and U.S. Pat. No. 5,654,003 (corresponding to Japanese Patent Publication JP-A-8-38138) disclose tablets using the above-mentioned shearform matrix.

All of the tablets explained in the above comprises saccharides, etc. as the main excipient, and they are porous tablets being capable of rapidly disintegrating, and produced by seeking how to increase the strength of tablets maintaining a porous property thereof, but they have problems such as complicated production procedures and in terms of the cost thereof, and hence, it has been desired to develop an excellent method in total aspects for producing an intrabuccally disintegrating tablet.

For example, the tablets obtained by a method disclosed in the above U.S. Pat. No. 4,371,516 (corresponding Japanese Patent Publication JP-B-62-50445) have weak strength, and they may have problems when pushed out from PTP. Moreover, said method has complicated production procedures, and requires additional equipment, and hence, it is not advantageous in view of the cost. On the other hand, although the tablets obtained by the method disclosed in WO 93-12769 have improved strength, said method has also complicated production procedures as the method disclosed in U.S. Pat. No. 4,371,516 (corresponding Japanese Patent Publication JP-B-62-50445) does, and hence, it is not advantageous in view of the cost.

Moreover, in the wet-tabletting methods disclosed in the above, wet powders tend to adhere to a die or a punch when tabletting, and it is also necessary to use an additional device to provide a prescribed amount of wet powders to the die, and hence, those methods are not suitable for continuous tabletting. Therefore, it becomes necessary to improve a tabletting machine per se in order to overcome these problems (see, JP-A-8-19589 and JP-A-8-19590).

Further, in the above-mentioned humidification methods, they need an additional step for humidifying tablets other than the conventional steps for producing tablets. In addition, these methods are not applicable to medicaments, which are unstable to humidity or tends to deliquesce under high humidity. Furthermore, the above-mentioned heat-melting methods also have problems such as that those methods are not applicable to medicaments being unstable to heat, or being incompatible with water-soluble meltable binders.

SUMMARY OF THE INVENTION

The present inventors have intensively studied in order to overcome the problems in the conventional methods, and have found an economically excellent method for producing an excellent intrabuccally disintegrating tablet having strength sufficient to take it out from a Press Through Pack and not to cause problems for the handling, as well as being capable of rapidly disintegrating in the oral cavity, by a conventional wet granulation using a solution prepared by dissolving a saccharide having a high solubility in water and a water-soluble binder in water.

According to the present invention, a method for producing an intrabuccally disintegrating tablet which comprises the following Steps (a), (b) and (c), wherein a medicament is mixed before granulation or tabletting:

(a) a step of dissolving at least one saccharide having a high solubility in water and at least one water-soluble binder in water alone or in water and an alcohol;

(b) a step of mixing the solution obtained in the above Step (a) with at least one excipient, granulating, drying and tabletting the mixture under a low compression pressure;

(c) a step of aging the tablets obtained in the above Step (b), and an intrabuccally disintegrating tablet produced by the above method are provided.

DETAILED DESCRIPTION OF THE INVENTION

The terms used in the present specification are explained below.

In the present specification, the term "saccharide having a high solubility in water" means a saccharide having relatively such a property among the so-called saccharides, and means ones having a solubility of about 40 g to about 250 g at about 25° C. in 100 ml of purified water (hereinafter, occasionally simply referred to as "solubility", and the measurement of solubility is explained hereinbelow). These saccharides (hereinafter, occasionally referred to "the saccharide used in the present invention") include, for example, a monosaccharide such as glucose, xylose [solubility: about 125 g; Merck Index, 12th ed., 10220 (1996)], a sugar alcohol such as xylitol, sorbitol, erythritol, and a disaccharide such as sucrose (white sugar), but erythritol, xylitol and sucrose are preferable. These saccharides can be used alone or in a mixture of two or more of these saccharides, and can usually be contained in an amount of about 0.1 to about 20% by weight, preferably in an amount of about 0.5 to about 10% by weight in the present tablet.

Thus, in the present specification, for example, mannitol and lactose have a low solubility as shown in Examples as disclosed below, and cannot fall in the category of the "saccharide having a high solubility in water" of the present invention, and they are regarded as saccharides outside the saccharides used in the present invention.

The water-soluble binder includes ones which can be dissolved together with the saccharides used in the present invention in water alone or in water and an alcohol (cf. ethanol), and then, can exhibit a desired binding property, for example, polyvinylpyrrolidone, pullulan, hydroxypropylcellulose, hydroxypropylmethylcellulose, acacia, water-soluble gelatin, etc., and polyvinylpyrrolidone is preferable. These water-soluble binders can be used alone or in a mixture of two or more of these water-soluble binders, and can usually be contained in an amount of about 0.1 to about 20% by weight, preferably in an amount of about 0.5 to about 5% by weight in the present tablet.

Corn starch is usually used as a binder, but the dissolving rate thereof in water is low, and as a result, a tablet being prepared by using thereof shows the delay in disintegration, and hence, corn starch cannot be used as the above-mentioned water-soluble binder in the present invention.

The excipient may usually be saccharides other than saccharides used in the present invention, for example, mannitol, lactose, mannose, but the saccharides used in the present invention can also be used as an excipient.

The intrabuccally disintegrating tablets of the present invention can be applied to any medicaments which can be formulated by a conventional wet granulation or by a conventional fluidized bed granulation, for example, citrate or citrate dihydrate of mosapride disclosed in U.S. Pat. No. 4,870,074 (chemical name: (±)-4-amino-5-chloro-2-ethoxy-N-[[4-(p-fluorobenzyl)-2-morpholinyl]methyl]benzamide) (hereinafter, simply referred to as "mosapride citrate"), alacepril (Merck Index 11th ed., 192), brotizolam (Merck Index, 11th ed., 1439), hydrochloride or tannate of berberine (Merck Index, 11th ed., 1169), and loperamide hydrochloride (Merck Index, 11th ed., 5450). The medicament can be mixed before either granulation or tabletting, and it is preferably mixed before granulation or tabletting in Step (b), more preferably before granulation in Step (b). The medicament may usually be contained in an amount of about 0.01 to about 20% by weight, preferably in an amount of about 0.1 to about 10% by weight in the present tablet.

The intrabuccally disintegrating tablet of the present invention may additionally contain a sweetening agent or a flavor in order to improve a feeling when taken, if necessary. Besides, the intrabuccally disintegrating tablet of the present invention may additionally contain a lubricant or a disintegrator which are usually necessary for conventional formulation procedures.

The tabletting procedure under a low compression pressure in Step (b) is usually carried out under a pressure of about 20 to about 300 kg/cm$^2$, preferably under a pressure of about 50 to about 200 kg/cm$^2$.

The drying procedure in Step (b) is preferably carried out until the surface of granules becomes dry. By the above drying, preferable flowing properties of granules are obtained.

The tablets obtained in the above Step (b) are subjected to aging in Step (c).

The "aging" means a step of making a pharmaceutical property of tablets, etc. to be stationary state, by which an intrabuccally disintegrating tablets having a desired strength can be obtained. The aging is usually carried out by allowing compositions to stand at room temperature (preferably at a temperature higher than about 15° C.) for several hours to about several days, or as a positive aging, by warming compositions at a temperature higher than room temperature, preferably at a temperature higher than about 30° C. for about 10 seconds to several days. The positive aging is preferably carried out by warming compositions at a temperature higher than about 40° C. but lower than a softening point of a water-soluble binder used in the present invention, more preferably at a temperature of from about 40° C. to about 80° C., for about 1 minute to about 3 days, more preferably for about 1 minute to about 24 hours. In addition, any treatments for making the tablets etc. to be stationary state other than the methods disclosed herein can also be included in the aging procedure of the present invention.

The "softening point" means a temperature, at which a solid substance starts to soften, and can easily deform, for example, the softening point of polyvinylpyrrolidone is about 150° C., and that of hydroxypropylcellulose is about 130° C.

The weight of the tablets produced by the present invention may not be specified, but it is usually in the range of about 50 mg to about 500 mg, preferably in the range of about 100 mg to about 400 mg, more preferably in the range of about 150 mg to about 300 mg.

The following embodiments may be exemplified as a preferable method for producing the intrabuccally disintegrating tablets of the present invention.

A method for producing an intrabuccally disintegrating tablet, comprising the following Steps (a'), (b') and (c'), wherein a medicament is mixed before granulation or tabletting.

(a'): a step of dissolving at least one saccharide selected from the group consisting of erythritol, xylitol, sorbitol, glucose and sucrose in an amount of about 0.5 to about 10% by weight, and at least one water-soluble binder selected from the group consisting of polyvinylpyrrolidone, pullulan, hydroxypropylcellulose, hydroxypropylmethylcellulose and water-soluble gelatin in an amount of about 0.5 to about 5% by weight, in water alone or in water and ethanol;

(b'): a step of mixing the solution obtained in the above Step (a') with at least one excipient, granulating, drying, and compressing the mixture under a low compression pressure of about 50 to about 200 kg/cm$^2$;

(c'): a step of aging the tablets obtained in the above Step (b') at a temperature lower than a softening point of the water-soluble binder used in the above (a') but higher than about 400 for about 1 minute to about 24 hours;

The method of the present invention will be illustrated in more detail below.

A saccharide used in the present invention and a water-soluble binder are dissolved in water alone, if necessary, or with adding thereto an alcohol, and an excipient is added to the solution obtained above, and further the mixture is dried after wet kneading granulation; or a saccharide used in the present invention and a water-soluble binder are dissolved in water alone, if necessary, or with adding thereto an alcohol, and the solution thus obtained is subjected to fluidized bed granulation by spraying the mixture onto a fluidized excipient, and then the granules thus obtained are dried, to give a co-dissolved mixture of the saccharide used in the present invention and the water-soluble binder. The co-dissolved mixture is in semi-solid state and can distribute uniformly in the granules, but the surface of granules is in dry state. A medicament may be added before either granulation or tabletting, but as mentioned above, a medicament is preferably added before granulation or tabletting in Step (b). Then, the granules containing said medicament or a mixture of a medicament and the granules are compressed under a low compression pressure of about 20 to about 300 kg/cm$^2$ to give porous tablets. The porous tablets thus obtained are still not satisfactory because they can rapidly disintegrate in the oral cavity but the strength thereof is not sufficient enough. However, these tablets can be solidified by aging, for example, by allowing them to stand at room temperature for several hours to several days, or by warming them at a temperature higher than room temperature for a dozen seconds to several days, preferably at a temperature lower than a softening point of the water-soluble binder to be used but higher than about 40° C. for about 1 minute to about 24 hours. The tablets solidified by allowing to stand under the conventional conditions or by a conventional positive aging as mentioned above have high strength being sufficient for the handling, as well as they can rapidly disintegrate in the oral cavity.

The tablets of the present invention, the methods for producing thereof, and the excellent properties of the present tablets are illustrated by the following Examples and Reference Examples, but the present invention should not be construed to be limited thereto. In addition, a method for measuring the solubility of saccharides used in the present invention is also explained below.

EXAMPLE 1

TABLE 1

| Components | Weight | % by weight |
|---|---|---|
| Sorbitol | 4 mg | 2% |
| Polyvinylpyrrolidone | 4 mg | 2% |
| Mannitol (excipient) | q.s. | |
| Mosapride citrate | 5 mg | 2.5% |
| Magnesium stearate | 1 mg | |
| Totally | 200 mg | |

Polyvinylpyrrolidone (K30, 4 g, manufactured by BASF Aktiengesellschaft) and sorbitol (4 g, solubility: about 130 g, manufactured by Nacalai Tesque) were mixed in a mortar, and thereto was added water (10 g), and then further added ethanol (15 g) to dissolve the mixture therein. Mannitol (q.s., solubility: about 18.5 g, manufactured by Kao Corporation) and mosapride citrate (5 g) were put into a polyethylene-made bag and mixed. The mixture was put into a mortar, and thereto was added the solution obtained above. The mixture was kneaded, and dried in a box drier at 50° C. for 16 hours. The mixture was screened through a 24 mesh sieve for sizing, and thereto was added magnesium stearate. The mixture was put into a polyethylene-made bag, and mixed therein to give granules for tabletting. The mixture was compressed on a single-punch tabletting machine (Type 2B, manufactured by KIKUSUI SEISAKUSHO LTD.) to give tablets having a diameter of 8.0 mm and a hardness of 0.5 kg. The resulting tablets were subjected to aging at room temperature for 3 days to give intrabuccally disintegrating tablets weighing 200 mg each.

EXAMPLE 2

Using the same prescription (Table 1) as Example 1, the components were compressed and tabletted in the same manner as in Example 1. The resulting tablets were subjected to aging at 70° C. for 6 hours to give intrabuccally disintegrating tablets weighing 200 mg each.

EXAMPLE 3

TABLE 2

| Components | Weight | % by weight |
|---|---|---|
| Xylitol | 4.5 mg | 1.5% |
| Polyvinylpyrrolidone | 4.5 mg | 1.5% |
| Mannitol (excipient) | q.s. | |
| Alacepril | 12.5 mg | 4.2% |
| L-Menthol | 1 mg | |
| Magnesium stearate | 1.5 mg | |
| Totally | 300 mg | |

Using a fluidized bed granulator (Flow Coater: type FLO-5, manufactured by Freund Industrial Co., Ltd.), alacepril (125 g) and mannitol (q.s., solubility: about 18.5 g, manufactured by Kao Corporation) were fluidized, and thereto was sprayed a solution of polyvinylpyrrolidone (K30, 45 g, manufactured by BASF Aktiengesellschaft) and xylitol (45 g, solubility: about 135 g, manufactured by Eisai Co. Ltd.) in a mixture of water-ethanol (1:1, 1000 g) for granulation, and subsequently, the mixture was dried in a fluidized bed. The mixture was subjected to sizing with a twin rotor equipped with a 32 mesh screen, and thereto were added L-menthol (10 g) and magnesium stearate (15 g). The resulting mixture was blended in a V-blender to give granules for tabletting. The mixture was compressed on a rotary tabletting machine (Cleanpress C19, manufactured by KIKUSUI SEISAKUSHO LTD.) to give tablets having a diameter of 9.5 mm and a hardness of 0.5 kg. Further, the resulting tablets thus obtained were subjected to aging at room temperature for 3 days to give intrabuccally disintegrating tablets weighing 300 mg each.

EXAMPLE 4

Using the same prescription (Table 2) of Example 3, the components were tabletted in the same manner as in Example 3, and the resulting tablets were subjected to aging at 70° C. for 3 hours to give intrabuccally disintegrating tablets weighing 300 mg each.

EXAMPLE 5

TABLE 3

| Components | Weight | % by weight |
| --- | --- | --- |
| Xylitol | 4.5 mg | 1.5% |
| Hydroxypropylcellulose | 3 mg | 1% |
| Mannitol (excipient) | q.s. | |
| Mosapride citrate | 5 mg | 1.7% |
| L-Menthol | 1 mg | |
| Magnesium stearate | 1.5 mg | |
| Totally | 300 mg | |

According to the prescription of Table 3, xylitol (45 g, solubility: about 135 g, manufactured by Eisai Co., Ltd.), hydroxypropylcellulose (L, 30 g, manufactured by NISSO, Ltd.) were dissolved in a mixture of water and ethanol (1:1, 1500 g), and the mixture was treated in the same manner as in Example 3 to give tablets having a hardness of 0.2 kg. The resulting tablets were subjected to aging at room temperature for 3 days, to give intrabuccally disintegrating tablets weighing 300 mg each.

EXAMPLE 6

TABLE 4

| Components | Weight | % by weight |
| --- | --- | --- |
| Erythritol | 6 mg | 2% |
| Polyvinylpyrrolidone | 9 mg | 3% |
| Mannitol (excipient) | q.s. | |
| Mosapride citrate | 5 mg | 1.7% |
| L-Menthol | 1 mg | |
| Magnesium stearate | 1.5 mg | |
| Totally | 300 mg | |

Polyvinylpyrrolidone (PVP, K30, 90 g, manufactured by BASF Aktiengesellschaft) and erythritol (60 g, solubility: about 47.5 g, manufactured by NIKKEN CHEMICALS CO., LTD.) were mixed in a beaker, and the mixture was dissolved in water (150 g), and thereto was further added ethanol (200 g). Mannitol (q.s., solubility: about 18.5 g, manufactured by Kao Corporation) and mosapride citrate (50 g) were blended in a high-shear granulator (Vertical Granulator VG25, manufactured by POWLEX CORPORATION), and thereto was added the above solution of PVP and erythritol. The mixture was stirred for granulation for 5 minutes. The mixture was sieved in a flash mill, and dried in a box fan drier for 16 hours. After drying, the mixture was screened through a 24 mesh sieve for sizing, and thereto were added L-menthol (10 g) and magnesium stearate (15 g). The mixture was blended in a V-blender to give granules for tabletting. The granules were compressed on a rotary tabletting machine (Cleanpress C19, manufactured by KIKUSUI SEISAKUSHO LTD.) to give tablets having a hardness of 0.5 kg. Further, the resulting tablets were subjected to aging at 50° C. for 12 hours to give intrabuccally disintegrating tablets weighing 300 mg each.

EXAMPLE 7

TABLE 5

| Components | Weight | % by weight |
| --- | --- | --- |
| Glucose | 9 mg | 3% |
| Pullulan | 1.5 mg | 0.5% |
| Mannitol (excipient) | q.s. | |
| Mosapride citrate | 5 mg | 1.7% |
| L-Menthol | 1 mg | |
| Magnesium stearate | 1.5 mg | |
| Totally | 300 mg | |

According to the prescription of Table 5, glucose (90 g, solubility: about 75 g, manufactured by Wako Pure Chemical Industries, Ltd.) and pullulan (PI-20, 15 g, manufactured by HAYASHIBARA) were dissolved in water (150 g), and the mixture was treated in the same manner as in Example 6 to give tablets having a hardness of 0.3 kg. The resulting tablets were subjected to aging at 70° C. for 3 hours to give intrabuccally disintegrating tablets weighing 300 mg each.

EXAMPLE 8

TABLE 6

| Components | Weight | % by weight |
| --- | --- | --- |
| Erythritol | 3 mg | 1% |
| Hydroxypropylmethylcellulose | 3 mg | 1% |
| Erythritol (excipient) | q.s. | |
| Mosapride citrate | 5 mg | 1.7% |
| Magnesium stearate | 1.5 mg | |
| Totally | 300 mg | |

According to the prescription of Table 6, hydroxypropylmethylcellulose (HPMC (TC-5R), 30 g, manufactured by SHIN-ETSU CHEMICAL CO., LTD.) and erythritol (30 g, solubility: about 47.5 g, manufactured by NIKKEN CHEMICALS CO., LTD.) were dissolved in water (150 g), and thereto was added ethanol (200 g) to dissolve the mixture therein. The mixture was treated in the same manner as in Example 6 to give tablets having a hardness of 0.3 kg. Further, the resulting tablets were subjected to aging at 70° C. for 3 hours to give intrabuccally disintegrating tablets weighing 300 mg each.

EXAMPLE 9

TABLE 7

| Components | Weight | % by weight |
| --- | --- | --- |
| Erythritol | 6 mg | 2% |
| Polyvinylpyrrolidone | 15 mg | 5% |
| Mannitol (excipient) | q.s. | |
| Mosapride citrate | 5 mg | 1.7% |

TABLE 7-continued

| Components | Weight | % by weight |
|---|---|---|
| L-Menthol | 1 mg | |
| Magnesium stearate | 3 mg | |
| Totally | 300 mg | |

According to the prescription of Table 7, erythritol (60 g, solubility: about 47.5 g, manufactured by NIKKEN CHEMICALS CO., LTD.), polyvinylpyrrolidone (K30, 150 g, manufactured by BASF Aktiengesellschaft) were dissolved in a mixture of water-ethanol (1:1, 2000 g), and the mixture was treated in the same manner as in Example 3 to give tablets having a hardness of 0.3 kg. Further, the resulting tablets were subjected to aging at 70° C. for 4 hours to give intrabuccally disintegrating tablets weighing 300 mg each.

EXAMPLE 10

TABLE 8

| Components | Weight | % by weight |
|---|---|---|
| Sucrose | 6 mg | 2% |
| Polyvinylpyrrolidone | 6 mg | 2% |
| Mannitol (excipient) | q.s. | |
| Mosapride citrate | 5 mg | 1.7% |
| L-Menthol | 1 mg | |
| Magnesium stearate | 3 mg | |
| Totally | 300 mg | |

According to the prescription of Table 8, sucrose (60 g, solubility: about 170 g, manufactured by Dai-Nippon Meiji Sugar Co., Ltd.) and polyvinylpyrrolidone (K30, 60 g, manufactured by BASF Aktiengesellschaft) were dissolved in a mixture of water-ethanol (1:1, 1500 g), and the mixture was treated in the same manner as in Example 3 to give tablets having a hardness of 0.3 kg. Further, the resulting tablets were subjected to aging at 70° C. for 4 hours to give intrabuccally disintegrating tablets weighing 300 mg each.

EXAMPLE 11

TABLE 9

| Components | Weight | % by weight |
|---|---|---|
| Erythritol | 6 mg | 2% |
| Polyvinylpyrrolidone | 6 mg | 2% |
| Mannitol (excipient) | q.s. | |
| Mosapride citrate | 5 mg | 1.7% |
| L-Menthol | 1 mg | |
| Magnesium stearate | 3 mg | |
| Totally | 300 mg | |

According to the prescription of Table 9, erythritol (60 g, solubility: about 47.5 g, manufactured by NIKKEN CHEMICALS CO., LTD.) and polyvinylpyrrolidone (K30, 60 g, manufactured by BASF Aktiengesellschaft) were dissolved in a mixture of water-ethanol (1:1, 2000 g), and the mixture was treated in the same manner as in Example 3 to give tablets having a hardness of 0.3 kg. Further, the resulting tablets were subjected to aging at 80° C. for 2 minutes to give intrabuccally disintegrating tablets weighing 300 mg each.

EXAMPLE 12

TABLE 10

| Components | Weight | % by weight |
|---|---|---|
| Erythritol | 30 mg | 10% |
| Polyvinylpyrrolidone | 6 mg | 2% |
| Mannitol (excipient) | q.s. | |
| Berberine tannate | 5 mg | 10% |
| L-Menthol | 1 mg | |
| Magnesium stearate | 3 mg | |
| Totally | 300 mg | |

According to the prescription of Table 10, erythritol (30 g, solubility: about 47.5 g, manufactured by NIKKEN CHEMICALS CO., LTD.) and polyvinylpyrrolidone (K30, 60 g, manufactured by BASF Aktiengesellschaft) were dissolved in a mixture of water-ethanol (1:1, 1500 g), and the mixture was treated in the same manner as in Example 3 to give tablets having a hardness of 0.5 kg. Further, the resulting tablets were subjected to aging at 70° C. for 4 hours to give intrabuccally disintegrating tablets weighing 300 mg each.

EXAMPLE 13

TABLE 11

| Components | Weight | % by weight |
|---|---|---|
| Sucrose | 2 mg | 1% |
| Polyvinylpyrrolidone | 4 mg | 2% |
| Water-soluble gelatin | 2 mg | 1% |
| Mannitol (excipient) | q.s. | |
| Brotizolam | 0.25 mg | 0.13% |
| L-Menthol | 1 mg | |
| Magnesium stearate | 2 mg | |
| Totally | 200 mg | |

According to the prescription of Table 11, the components were treated in the same manner as in Example 3 except for that brotizolam was dissolved together with a binder in a mixed solvent for granulation, and the mixture was tabletted under a compression pressure of 120 kg/cm$^2$ to give tablets having a diameter of 9.0 mm and a hardness of 0.1 kg. Further, the resulting tablets were subjected to aging at 70° C. for 5 minutes to give intrabuccally disintegrating tablets weighing 200 mg each.

EXAMPLE 14

TABLE 12

| Components | Weight | % by weight |
|---|---|---|
| Sucrose | 1.8 mg | 1% |
| Polyvinylpyrrolidone | 3.6 mg | 2% |
| Neusilin | 5 mg | 2.8% |
| Mannitol (excipient) | q.s. | |
| Erythritol (excipient) | 36 mg | |
| Asparateam | 0.9 mg | |
| Loperamide hydrochloride | 0.25 mg | 0.14% |
| Berberine tannate | 37.5 mg | |
| Magnesium stearate | 2 mg | |
| Totally | 180 mg | |

According to the prescription of Table 12, the components were treated in the same manner as in Example 3 to give tables having a diameter of 8.5 mm and a hardness of 0.2 kg. The resulting tablets were subjected to aging at 70° C. for 5 minutes to give intrabuccally disintegrating tablets weighing 180 mg each.

Reference Example 1
Under Conditions Wherein Those in Step (a) Were not Satisfied

TABLE 13

| Components | Weight | % by weight |
| --- | --- | --- |
| Erythritol | 4 mg | 2% |
| Polyvinylpyrrolidone | 4 mg | 2% |
| Mannitol (excipient) | q.s. | |
| Mosapride citrate | 5 mg | 2.5% |
| Magnesium stearate | 1 mg | |
| Totally | 200 mg | |

Polyvinylpyrrolidone (PVP (K30), 40 g, manufactured by BASF Aktiengesellschaft) was dissolved in a mixture of water (10 g) and ethanol (15 g). Separately, mannitol (q.s., solubility: about 18.5 g, manufactured by Kao. Corporation), erythritol (40 g, solubility: about 47.5 g, manufactured by NIKKEN CHEMICALS CO., LTD.), and mosapride citrate (50 g) were blended in a polyethylene-made bag, and the mixture was put into a mortar, and thereto was added the above PVP-ethanol solution. The mixture was kneaded with a pestle, and dried in a box fan drier at 50° C. for 16 hours. The mixture was screened through a 24 mesh sieve for sizing, and to the resultant was added magnesium stearate (10 g). The mixture was blended in a polyethylene-made bag to give granules for tabletting. The granules were compressed on a single-punch tabletting machine (Type 2B, manufactured by KIKUSUI SEISAKUSHO LTD.) to give tablets having a hardness of 0.5 kg. The resulting tablets were subjected to aging at room temperature for 3 days to give intrabuccally disintegrating tablets weighing 200 mg each.

Reference Example 2
Under Conditions Wherein Those in Step (a) Were not Satisfied The granules for tabletting obtained in Reference Example 1 were compressed on a single-punch tabletting machine (Type 2B, manufactured by KIKUSUI SEISAKUSHO LTD.) to give tablets having a hardness of 0.5 kg. The resulting tablets were subjected to aging at 70° for 3 hours to give intrabuccally disintegrating tablets weighing 200 mg each.

Reference Example 3
Under Conditions Wherein Those in Step (a) Were not Satisfied Reference Example 3 was carried out using the same prescription of Table 13 in Reference Example 1. Namely, erythritol (40 g, solubility: about 47.5 g, manufactured by NIKKEN CHEMICALS CO., LTD.) was dissolved in water (10 g) and ethanol (15 g). Separately, mannitol (q.s., solubility: about 18.5 g, manufactured by Kao Corporation), polyvinylpyrrolidone (PVP (K30), 40 g, manufactured by BASF Aktiengesellschaft) and mosapride citrate (50 g) were blended in a polyethylene-made bag, and the mixture was put into a mortar, and thereto was added the above erythritol-ethanol solution. The mixture was kneaded with a pestle, and dried in a box fan drier at 50° C. for 16 hours. The mixture was screened through a 24 mesh sieve for sizing, and to the resultant was added magnesium stearate (10 g). The mixture was blended in a polyethylene-made bag to give granules for tabletting. The granules were compressed on a single-punch tabletting machine (Type 2B, manufactured by KIKUSUI SEISAKUSHO LTD.) to give tablets having a hardness of 0.5 kg. The resulting tablets were subjected to aging at 70° C. for 3 hours to give intrabuccally disintegrating tablets weighing 200 mg each.

Reference Example 4
Under the Conditions Wherein Those in Step (a) Were not Satisfied The granules for tabletting obtained in Reference Example 3 were compressed on a single-punch tabletting machine (Type 2B, manufactured by KIKUSUI SEISAKUSHO LTD.) to give tablets having a hardness of 3.0 kg. The resulting tablets were subjected to aging at 70° for 3 hours to give intrabuccally disintegrating tablets weighing 200 mg each.

Reference Example 5
Under the Conditions Wherein a Saccharide Used in Step (a) was Improper

TABLE 14

| Components | Weight | % by weight |
| --- | --- | --- |
| Lactose | 4 mg | 2% |
| Polyvinylpyrrolidone | 4 mg | 2% |
| Mannitol (excipient) | q.s. | |
| Mosapride citrate | 5 mg | 2.5% |
| Magnesium stearate | 1 mg | |
| Totally | 200 mg | |

Polyvinylpyrrolidone (PVP (K30), 40 g, manufactured by BASF Aktiengesellschaft) and lactose (40 g, solubility: about 13.5 g, manufactured by DMV International) were dissolved in water (10 g) and ethanol (15 g). Separately, mannitol (q.s., solubility: about 18.5 g, manufactured by Kao Corporation), and mosapride citrate (50 g) were blended in a polyethylene-made bag, and the mixture was put into a mortar, and thereto was added the above PVP-lactose solution. The mixture was kneaded with a pestle, and dried in a box fan drier at 50° C. for 16 hours. The mixture was screened through a 24 mesh sieve for sizing, and to the resultant was added magnesium stearate (10 g). The mixture was blended in a polyethylene-made bag to give granules for tabletting. The granules were compressed on a single-punch tabletting machine (Type 2B, manufactured by KIKUSUI SEISAKUSHO LTD.) to give tablets having a hardness of 0.5 kg. The resulting tablets were subjected to aging at 70° C. for 3 days to give intrabuccally disintegrating tablets weighing 200 mg each.

Reference Example 6
Under the Conditions Wherein a Saccharide Used in Step (a) was Improper

TABLE 15

| Components | Weight | % by weight |
| --- | --- | --- |
| Mannitol | 4 mg | 2% |
| Polyvinylpyrrolidone | 4 mg | 2% |
| Erythritol (excipient) | q.s. | |

TABLE 15-continued

| Components | Weight | % by weight |
|---|---|---|
| Mosapride citrate | 5 mg | 2.5% |
| Magnesium stearate | 1 mg | |
| Totally | 200 mg | |

Polyvinylpyrrolidone (PVP (K30), 40 g, manufactured by BASF Aktiengesellschaft) and mannitol (40 g, solubility: about 18.5 g, manufactured by Kao Corporation) were dissolved in water (10 g) and ethanol (15 g). Separately, erythritol (q.s., solubility: about 47.5 g, manufactured by NIKKEN CHEMICALS CO., LTD.), and mosapride citrate (50 g) were blended in a polyethylene-made bag, and the mixture was put into a mortar, and thereto was added the above PVP-mannitol solution. The mixture was kneaded with a pestle, and dried in a box fan drier at 50° C. for 16 hours. The mixture was screened through a 24 mesh sieve for sizing, and to the resultant was added magnesium stearate (10 g). The mixture was blended in a polyethylene-made bag to give granules for tabletting. The granules were compressed on a single-punch tabletting machine (Type 2B, manufactured by KIKUSUI SEISAKUSHO LTD.) to give tablets having a hardness of 3.0 kg. The resulting tablets were subjected to aging at 70° C. for 3 days to give intrabuccally disintegrating tablets weighing 200 mg each.

Reference Example 7
Under the Conditions Wherein a Binder was Improper

TABLE 16

| Components | Weight | % by weight |
|---|---|---|
| Erythritol | 4 mg | 2% |
| Corn starch | 3 mg | 1.5% |
| Mannitol (excipient) | q.s. | |
| Mosapride citrate | 5 mg | 2.5% |
| Magnesium stearate | 1 mg | |
| Totally | 200 mg | |

Corn starch (30 g, manufactured by NIHON SHOKUHIN KAKO CO., LTD.) was dispersed in water (30 ml) in a beaker, and the mixture was stirred at 80° C. for 15 minutes to give a starch glue, to which erythritol (40 g, solubility: about 47.5 g, manufactured by Nikken Chemicals Co., Ltd.) was dissolved, and then the mixture was cooled to 30° C. Separately, mannitol (q.s., solubility: about 18.5 g, manufactured by Kao Corporation), and mosapride citrate (50 g) were blended in a polyethylene-made bag, and the mixture was put into a mortar, and thereto was added the above erythritol-starch glue solution. The mixture was kneaded with a pestle, and dried in a box fan drier at 50° C. for 16 hours. The mixture was screened through a 24 mesh sieve for sizing, and to the resultant was added magnesium stearate (10 g). The mixture was blended in a polyethylene-made bag to give granules for tabletting. The granules were compressed on a single-punch tabletting machine (Type 2B, manufactured by KIKUSUI SEISAKUSHO LTD.) to give tablets having a hardness of 0.5 kg. The resulting tablets were subjected to aging at 70° C. for 3 hours to give intrabuccally disintegrating tablets weighing 200 mg each.

Reference Example 8
Under the Conditions Wherein the Drying Procedure in Step (b) was not Carried Out

TABLE 17

| Components | Weight | % by weight |
|---|---|---|
| Erythritol | 9 mg | 3% |
| Polyvinylpyrrolidone | 6 mg | 2% |
| Mannitol (excipient) | q.s. | |
| Mosapride citrate | 5 mg | 1.7% |
| Magnesium stearate | 3 mg | |
| Totally | 300 mg | |

Erythritol (9 g, solubility: about 47.5 g, manufactured by Nikken Chemicals Co., Ltd.) and polyvinylpyrrolidone (PVP (K30), 6 g, manufactured by BASF Aktiengesellschaft) were dissolved in water (10 g), and thereto was added ethanol (15 g). Mannitol (q.s., solubility: about 18.5 g, manufactured by Kao Corporation) and mosapride citrate (5 g) were blended in a polyethylene-made bag, and the mixture was put into a mortar, and thereto was added the above erythritol-PVP solution. The mixture was kneaded with a pestle. Although the resulting kneaded mixture of which surface was wet was tried to tablet with a single-punch tabletting machine (Type 2B, manufactured by KIKUSUI SEISAKUSHO LTD.), the kneaded mixture was adhered to the punch so that the continuous tabletting was not possible.

The disintegrating time in the oral cavity and the hardness of the tablets obtained in Examples 1–14 and in Reference Examples 1–8 are shown in Tables 18 and 19, respectively. In the following experiments on hardness and disintegrating properties, we evaluated tablets showing a hardness of over 2.5 kg, and a disintegrating time of within 30 minutes under the conditions as specified in the footnote of each Table, as a tablet fulfilling the subject tablet of the present invention.

TABLE 18

| Test item | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 | Ex. 13 | Ex. 14 |
|---|---|---|---|---|---|---|---|---|---|---|---|---|---|---|
| Disintegrating time[*1] | 18 sec. | 20 sec. | 20 sec. | 20 sec. | 25 sec. | 20 sec. | 25 sec. | 20 sec. | 25 sec. | 20 sec. | 15 sec. | 28 sec. | 18 sec. | 20 sec. |
| Hardness | 2.7 kg | 2.9 kg | 2.7 kg | 3.0 kg | 2.8 kg | 2.9 kg | 3.0 kg | 2.8 kg | 4.0 kg | 2.7 kg | 2.5 kg | 2.6 kg | 4.6 kg | 4.0 kg |

[*1]Disintegrating time means time for a tablet to disintegrate in the oral cavity by lightly touching it with the tongue without biting thereof, in five healthy adult male panellers.

*1): Disintegrating time means time for a tablet to disintegrate in the oral cavity by lightly touching it with the tongue without biting thereof, in five healthy adult male panellers.

TABLE 19

| Test item | Ref. Ex. 1 | Ref. Ex. 2 | Ref. Ex. 3 | Ref. Ex. 4 | Ref. Ex. 5 | Ref. Ex. 6 | Ref. Ex. 7 | Ref. Ex. 8 |
|---|---|---|---|---|---|---|---|---|
| Disintegrating time*1 | 12 sec. | 15 sec. | 15 sec. | >60sec. | 25 sec. | 60sec. | 50sec. | —*2 |
| Hardness | 0.7kg | 1.2kg | 0.6kg | 3.0 kg | 1.0kg | 3.2 kg | 1.0kg | —*2 |

*1Disintegrating time means time for a tablet to disintegrate in the oral cavity by lightly touching it with the tongue without biting thereof, in five healthy adult male panellers.
*2Undetectable because tablet could not be obtained due to adhering of the kneaded mixture to the punch.
Underlined: Items having problems.

*1): Disintegrating time means time for a tablet to disintegrate in the oral cavity by lightly touching it with the tongue without biting thereof, in five healthy adult male panellers.

*2): Undetectable because tablet could not be obtained due to adhering of the kneaded mixture to the punch.
Underlined: Items having problems.

As is shown in the above Tables 18 and 19, the tablets obtained in Examples 1–14 showed satisfactory values in the disintegrating time and the hardness thereof, but the tablets obtained in Reference Example 7 showed problems in both the disintegrating time and the hardness thereof, and the tablets obtained in other Reference Examples showed problems in either one of the disintegrating time and the hardness thereof, and they were improper.

Measurement of Solubility of Saccharides

Purified water at 25° C. (20 ml) was put into a beaker, and thereto was added each saccharide under stirring. Xylitol, sorbitol, glucose and sucrose were added in portions of 1 g, and erythritol was added in portions of 0.5 g, and lactose and mannitol were added in portions of 0.1 g, each. The mixture was stirred for one hour, and the dissolved amount of each saccharide was determined. The amount dissolving in 100 ml of water was converted and used as solubility of the saccharide in the present specification.

As explained in the above, the method of the present invention can be carried out without using any specific facility, and by which the desired intrabuccally disintegrating tablets can easily be produced in a large scale. Besides, the tablets produced by the method of the present invention are excellent intrabuccally disintegrating tablets which show good disintegrating property in the oral cavity as well as show enough strength being sufficient so that they do not disintegrate during the handling.

What is claimed is:

1. A method for producing an intrabuccally disintegrating tablet, which comprises the following Steps (a), (b) and (c), wherein a medicament is mixed at any stage of steps (a) or (b) before tabletting:
    (a) a step of dissolving at least one saccharide having a high solubility of about 40 g to about 250 g in 100 ml of purified water at about 25° C. and being selected from the group consisting of a monosaccharide, a sugar alcohol and a disaccharide and at least one water-soluble binder which is at least one member selected from the group consisting of polyvinylpyrrolidone, pullulan, hydroxypropylcellulose, hydroxypropylmethylcellulose, and water-soluble gelatin, in water alone or in water and an alcohol;
    (b) a step of mixing the solution obtained in the above Step (a) with at least one excipient, granulating, drying, and tabletting the mixture under a low compression pressure;
    (c) a step of aging the tablets obtained in the above Step (b).

2. A method for producing an intrabuccally disintegrating tablet, which comprises the following Steps (a), (b) and (c), wherein a medicament is mixed at any stage of steps (a) or (b) before tabletting:
    (a) a step dissolving at least one saccharide having a high solubility of about 40 g to about 250 g in 100 ml of purified water at about 25° C. and being selected from the group consisting of a monosaccharide, a sugar alcohol and a disaccharide and at least one water-soluble binder which is at least one member selected from the group consisting of polyvinylpyrrolidone, pullulan, hydroxypropylcellulose, hydroxypropylmethylcellulose, and water-soluble gelatin, in water alone or in water and an alcohol;
    (b) a step of mixing the solution obtained in the above Step (a) with at least one excipient, granulating, drying, and tabletting the mixture under a low compression pressure of about 20 to about 300 kg/cm$^2$;
    (c) a step of aging the tablets obtained in the above Step (b).

3. The method according to claim 2, wherein the aging procedure of Step (c) is carried out by warming the tablets obtained in Step (b) at a temperature higher than room temperature for about 1 minute to about 3 days.

4. The method according to claim 2, wherein the saccharide used in Step (a) is at least one member selected from the group consisting of erythritol, xylitol, sorbitol, glucose, and sucrose.

5. An intrabuccally disintegrating tablet which is produced by the following Steps (a), (b) and (c), wherein a medicament is mixed at any stage of steps (a) or (b) before tabletting:
    (a) A step of dissolving at least one saccharide having a high solubility of about 40 g to about 250 g in 100 ml of purified water at about 25° C. and being selected from the group consisting of a monosaccharide, a sugar alcohol and a disaccharide and at least one water-soluble binder which is at least one member selected from the group consisting of polyvinylpyrrolidone, pullulan, hydroxypropylcellulose, hydroxypropylmethylcellulose, and water-soluble gelatin, in water alone or in water and an alcohol;
    (b) a step of mixing the solution obtained in the above Step (a) with at least one excipient, granulating, drying, and tabletting the mixture under a low compression pressure;
    (c) a step of aging the tablets obtained in the above Step (b).

6. The method according to claim 1, wherein the amount of the saccharide used in Step (a) is in the range of about 0.5 to about 10% by weight to the total weight of the tablet.

7. The method according to claim 6, wherein the amount of the water-soluble binder is in the range of about 0.5 to about 5% by weight to the total weight of the tablet.

8. The method according to claim 7, wherein the aging procedure of Step (c) is carried out by warming, and the temperature for said warming is a temperature lower than a softening point of the water-soluble binder used in Step (a), but higher than about 40° C., and the aging period is in the range of about 1 minute to about 24 hours.

9. The method according to claim 2, wherein a medicament is mixed before granulation or tabletting in Step (b).

10. The method according to claim 2, wherein the drying procedure of Step (b) is carried out until the surface of granules becomes dry.

11. The intrabuccally disintegrating tablet according to claim 5, wherein the medicament is mosapride citrate.

12. An intrabuccally disintegrating tablet which is produced by the following Steps (a), (b) and (c), wherein a medicament is mixed at any stage of steps (a) or (b) before tabletting;
  (a) a step of dissolving at least one saccharide having a high solubility of about 40 g to about 250 g in 100 ml of purified water at about 25° C. and being selected from the group consisting of a monosaccharide, a sugar alcohol and a disaccharide, and at least one water-soluble binder which is at least one member selected from the group consisting of polyvinylpyrrolidone, pullulan, hydroxypropylcellulose, hydroxypropylmethylcellulose, and water-soluble gelatin, in water alone or in water and an alcohol;
  (b) a step of mixing the solution obtained in the above Step (a) with at least one excipient, granulating, drying, and tabletting the mixture under a low compression pressure of about 20 to about 300 kg/cm$^2$;
  (c) a step of aging the tablets obtained in the above Step (b).

13. An intrabuccally disintegrating tablet which is produced by the following Steps (a), (b) and (c), wherein a medicament is mixed at any stage of steps (a) or (b) before tabletting:
  (a) a step of dissolving at least one saccharide having a high solubility of about 40 g to about 250 g in 100 ml of purified water at about 25° C. and being selected from the group consisting of a monosaccharide, a sugar alcohol and a disaccharide, and at least one water-soluble binder which is at least one member selected from the group consisting of polyvinylpyrrolidone, pullulan, hydroxypropylcellulose, hydroxypropylmethylcellulose, and water-soluble gelatin, in water alone or in water and an alcohol;
  (b) a step of mixing the solution obtained in the above Step (a) with at least one excipient, granulating, drying, and tabletting the mixture under a low compression pressure of about 20 to about 300 kg/cm$^2$;
  (c) a step of aging the tablets obtained in the above Step (b) by warming them at a temperature higher than room temperature for about 1 minute to about 3 days.

14. The intrabuccally disintegrating tablet according to claim 5, wherein the weight of the tablet is in the range of about 150 mg to about 300 mg.

15. The intrabuccally disintegrating tablet according to claim 12, wherein the weight of the tablet is in the range of about 150 mg to about 300 mg.

16. The intrabuccally disintegrating tablet according to claim 13, wherein the weight of the tablet is in the range of about 150 mg to about 300 mg.

17. The method for producing an intrabuccally disintegrating tablet according to claim 1, wherein the medicament is mosapride citrate.

18. The method for producing an intrabuccally disintegrating tablet according to claim 2, wherein the medicament is mosapride citrate.

19. The method for producing an intrabuccally disintegrating tablet according to claim 3, wherein the medicament is mosapride citrate.

20. The method for producing an intrabuccally disintegrating tablet according to claim 4, wherein the medicament is mosapride citrate.

21. The intrabuccally disintegrating tablet according to claim 16, wherein the medicament is mosapride citrate.

22. The method for producing an intrabuccally disintegrating tablet according to claim 6, wherein the medicament is mosapride citrate.

23. The method for producing an intrabuccally disintegrating tablet according to claim 7, wherein the medicament is mosapride citrate.

24. The method for producing an intrabuccally disintegrating tablet according to claim 8, wherein the medicament is mosapride citrate.

25. The method for producing an intrabuccally disintegrating tablet according to claim 9, wherein the medicament is mosapride citrate.

26. The method for producing an intrabuccally disintegrating tablet according to claim 10, wherein the medicament is mosapride citrate.

27. The intrabuccally disintegrating tablet according to claim 12, wherein the medicament is mosapride citrate.

28. The intrabuccally disintegrating tablet according to claim 13, wherein the medicament is mosapride citrate.

29. The intrabuccally disintegrating tablet according to claim 14, wherein the medicament is mosapride citrate.

30. The intrabuccally disintegrating tablet according to claim 15, wherein the medicament is mosapride citrate.

* * * * *